United States Patent [19]
Flam

[11] Patent Number: 5,513,627
[45] Date of Patent: May 7, 1996

[54] ESOPHAGEAL TRACHEAL INTUBATOR AIRWAY

[76] Inventor: Gary H. Flam, 2244 Robinhood, Houston, Tex. 77005

[21] Appl. No.: 380,015

[22] Filed: Jan. 27, 1995

[51] Int. Cl.⁶ ..................................................... A61B 1/01
[52] U.S. Cl. ............................. 128/200.26; 128/207.15; 604/96; 604/174; 604/23
[58] Field of Search ......................... 128/207.14, 207.15, 128/200.26, 206.26, 10, 11, 911, 912, 4, 15, 16; 604/96–103, 174, 23

[56] References Cited

U.S. PATENT DOCUMENTS

| | | | |
|---|---|---|---|
| 5,038,766 | 8/1991 | Parker | 128/200.26 |
| 5,042,469 | 8/1991 | Augustine | 128/200.26 |
| 5,174,283 | 12/1992 | Parker | 128/200.26 |
| 5,203,320 | 4/1993 | Augustine | 128/10 |
| 5,241,956 | 9/1993 | Brain | 128/207.15 |
| 5,303,697 | 4/1994 | Brain | 128/200.26 |
| 5,339,805 | 8/1994 | Parker | 128/200.26 |
| 5,355,879 | 10/1994 | Brain | 128/207.15 |
| 5,372,131 | 12/1994 | Heinen, Jr. | 128/207.15 |

*Primary Examiner*—Christopher A. Bennett
*Assistant Examiner*—Eric P. Raciti

*Attorney, Agent, or Firm*—Kenneth A. Roddy

[57] ABSTRACT

An esophageal tracheal intubator airway device which allows rapid blind access to the larynx and esophagus of a patient for lung ventilation, stomach suctioning, fiberscopic examination of the upper respiratory and upper gastrointestinal tracts, and passage of an endotracheal tube into the trachea. The device has a conical positioning element which conforms to the base of the throat beneath the epiglottis and an elongate tubular esophageal conduit which extends through the positioning element and rearwardly therefrom in an arcuate curve. The esophageal conduit is sized to allow passage of a gastric suction tube and related medical instruments therethrough into the patient's esophagus. A laryngeal channel extends inwardly from the positioning element proximal end and curves outwardly to define an opening through the side wall of the positioning element. The channel is sized to allow passage of a cuffed endotracheal tube and related medical instruments therethrough into the patient's larynx and trachea. An inflatable tubular ring secured to the positioning element side wall surrounds the opening and when inflated, forms a sealing relation around the patient's laryngeal inlet while causing the positioning element to back out relative to the throat a sufficient distance for a lip at its proximal end to lift the tip of the epiglottis up and out of the way of the side wall opening.

15 Claims, 4 Drawing Sheets

ESOPHAGEAL TRACHEAL INTUBATOR AIRWAY

BACKGROUND OF THE INVENTION

1. Field of the Invention

This invention relates generally to blind intubating devices, and more particularly to an esophageal tracheal intubator airway device that is placed in the oropharynx of a patient and seals around the laryngeal opening to prevent obstruction of the patient's airway and allow immediate ventilation of the lungs, passage of an endotracheal tube into the trachea, stomach suctioning, and fiberscopic examination of the upper respiratory and upper gastrointestinal tracts.

2. Brief Description of the Prior Art

If a patient is unconscious, either during general anesthesia or for any other reason, it is the first responsibility of the anesthesiologist or emergency medical provider to ensure adequate spontaneous or controlled ventilation of the patient through an unobstructed airway. Face mask ventilation with "chin lift" and "jaw thrust" maneuvers, oral airways, and laryngeal mask airways are used frequently for ventilation, and prevent the tongue and soft tissues of the throat from falling backward and obstructing the patient's airway.

Brain, U.S. Pat. Nos. 4,509,514, 4,995,388, and 5,297,547 disclose laryngeal mask airway devices which are conduits that are inserted into the throat and when properly positioned, terminate at the laryngeal inlet, thereby preventing the tongue and soft tissues of the throat from falling backward and obstructing airflow to and from the patient's lungs.

Unconscious patients who are believed to be at increased risk of vomiting and pulmonary aspiration (i.e. full stomach, gastroesophageal reflux, obesity, pregnancy, code situations), however, need more airway protection. A cuffed endotracheal tube is considered to be the best airway in this regard because the inflatable cuff forms a seal between the airway tube and the inside of the trachea, preventing any vomitus or secretions from passing around the tube and into the patient's lungs.

Endotracheal intubation is frequently performed by means of direct laryngoscopy. The practitioner extends the head of the patient on the neck, places the laryngoscope into the mouth, pulls the tongue and soft tissues up and out of the way to expose the larynx, and places the endotracheal tube through the larynx and into the trachea. Phillips, U.S. Pat. No. 3,856,001 discloses a typical illuminated laryngoscope blade used to pull the tongue and soft tissues up and out of the way to allow insertion of an endotracheal tube under direct vision.

Some patients, however, cannot be intubated by this method because of poor mouth opening, decreased neck mobility, or other anatomical abnormalities, but must have rapid establishment of an airway and suctioning of gastric contents. Various blind devices can be used to intubate such patients who cannot be intubated by direct laryngoscopy.

Kruger, U.S. Pat. No. 4,612,927 and Frankel, U.S. Pat. No. 4,825,858 disclose intubating guide and conduit devices which, when placed into the esophagus, allow tracheal intubation via positionally related portions of the above guides and conduits. They do not accommodate for the wide anatomical variations in distance between the larynx and esophagus, nor do they allow ease of tube placement, visual confirmation of tube placement, or ventilation during the process of intubation.

Frass, U.S. Pat. No. 4,688,568 discloses a combination (double lumen) tube which may be used for ventilation and stomach suction. These types of devices have many limitations. For example, they cannot be used in short, young patients, they are bulky and clumsy, do not always allow suction catheters to be passed through both lumens, create initial ambiguity over which lumen has gone where, are not as protective against secretion aspiration as standard endotracheal tubes, and are to be used only in emergency situations.

Laryngeal mask airways, as decribed above allow rapid ventilation, and can be used as conduits for endotracheal intubation, such as that disclosed in Brain, U.S. Pat. No. 5,303,697. All of these devices, however, have shortcomings in the areas of placement, ventilation, and endotracheal intubation. For example, the tip of the laryngeal mask airway will often curl over on itself, or impinge on the tip of the epiglottis and bend it posteriorly, both of which prevent proper placement of the laryngeal mask airway over the laryngeal inlet. Also, the tip of the epiglottis may obstruct the lumen of the laryngeal mask airway and prevent adequate ventilation and intubation. In addition, the bands at the entrance to the laryngeal mask airway severely limit the size of the endotracheal tube that can be placed through it. Lastly, once the endotracheal tube is placed in the trachea, the laryngeal mask airway must be gently pulled out around the tube while maintaining its position in the trachea, which requires additional time and manipulations.

Other devices for rapid blind endotracheal intubation are known. Parker, U.S. Pat. No. 5,174,283 discloses an anatomically contoured guide element which is supposed to align itself about and atop the patient's larynx, allowing subsequent intubation. However, this device would be unusable in many patients because of the very wide range of anatomic variations between patients, particularly in epiglottis length and laryngeal shape and size. Also, this device does not provide a seal around the larynx to allow positive pressure ventilation without endotracheal intubation.

The present invention overcomes these problems and is distinguished over the prior art in general, and these patents in particular by an esophageal tracheal intubator airway device which allows rapid blind access to the larynx and esophagus of a patient for lung ventilation, stomach suctioning, fiberscopic examination of the upper respiratory and upper gastro-intestinal tracts, and passage of an endotracheal tube into the trachea. The device has a conical positioning element which conforms to the base of the throat beneath the epiglottis and an elongate tubular esophageal conduit which extends through the positioning element and rearwardly therefrom in an arcuate curve. The esophageal conduit is sized to allow passage of a gastric suction tube and related medical instruments therethrough into the patient's esophagus. A laryngeal channel extends inwardly from the positioning element proximal end and curves outwardly to define an opening through the side wall of the positioning element. The channel is sized to allow passage of a cuffed endotracheal tube and related medical instruments therethrough into the patient's larynx and trachea. An inflatable tubular member or ring secured to the positioning element side wall surrounds the opening and when inflated, forms a sealing relation around the patient's laryngeal inlet while causing the positioning element to back out relative to the throat a sufficient distance for a lip at its proximal end to lift the tip of the epiglottis up and out of the way of the side wall opening.

SUMMARY OF THE INVENTION

It is therefore an object of the present invention to provide an esophageal tracheal intubator airway device which facilitates ventilation of a patient and passage therethrough of endotracheal or esophageal tubular members and other elongate tubular instruments.

It is another object of this invention to provide an extremely versatile esophageal tracheal intubator airway device which allows immediate ventilation of the lungs, passage of a loaded endotracheal tube into the trachea, stomach suctioning, and fiberscopic examination of the upper respiratory and upper gastrointestinal tracts.

Another object of this invention is to provide an esophageal tracheal intubator airway device which is placed in the oropharynx of a patient and seals around the laryngeal opening to prevent obstruction of the patient's airway.

Another object of this invention is to provide an esophageal tracheal intubator airway device suitable for use in mask ventilation during short periods of anesthesia which will reduce the risk of patient vomiting and aspiration.

Another object of this invention is to provide an esophageal tracheal intubator airway device which can be loaded with an endotracheal tube and inserted into the pharynx of a patient and used for mask ventilation.

Another object of this invention is to provide an esophageal tracheal intubator airway device which can be loaded with an endotracheal tube and inserted into the pharynx of a patient and provide effective ventilation before, during, and after endotracheal intubation.

Another object of this invention is to provide an esophageal tracheal intubator airway device which can be loaded with an endotracheal tube and inserted into the pharynx of a patient and can be either left in place or removed after advancing the endotracheal tube into proper position within the patient's trachea.

Another object of this invention is to provide an esophageal tracheal intubator airway device which allows passage of elongate medical instruments and tubes for either fiberoptic guided or blind endotracheal intubation in situations where both direct and indirect laryngoscopy have failed.

A further object of this invention is to provide an esophageal tracheal intubator airway device which allows passage of elongate medical instruments to allow fiberoptic examination and biopsy of the patient's upper respiratory or upper gastrointestinal tracts.

A still further object of this invention is to provide an esophageal tracheal intubator airway device which is simple in construction, economical to manufacture, and safe and reliable in use.

Other objects of the invention will become apparent from time to time throughout the specification and claims as hereinafter related.

The above noted objects and other objects of the invention are accomplished by an esophageal tracheal intubator airway device which allows rapid blind access to the larynx and esophagus of a patient for lung ventilation, stomach suctioning, fiberscopic examination of the upper respiratory and upper gastrointestinal tracts, and passage of an endotracheal tube into the trachea. The device has a conical positioning element which conforms to the base of the throat beneath the epiglottis and an elongate tubular esophageal conduit which extends through the positioning element and rearwardly therefrom in an arcuate curve. The esophageal conduit is sized to allow passage of a gastric suction tube and related medical instruments therethrough into the patient's esophagus. A laryngeal channel extends inwardly from the positioning element proximal end and curves outwardly to define an opening through the side wall of the positioning element. The channel is sized to allow passage of a cuffed endotracheal tube and related medical instruments therethrough into the patient's larynx and trachea. An inflatable tubular ring secured to the positioning element side wall surrounds the opening and when inflated, forms a sealing relation around the patient's laryngeal inlet while causing the positioning element to back out relative to the throat a sufficient distance for a lip at its proximal end to lift the tip of the epiglottis up and out of the way of the side wall opening.

DESCRIPTION OF THE PREFERRED EMBODIMENT

Figures 1, 2, 3, 4, 5:
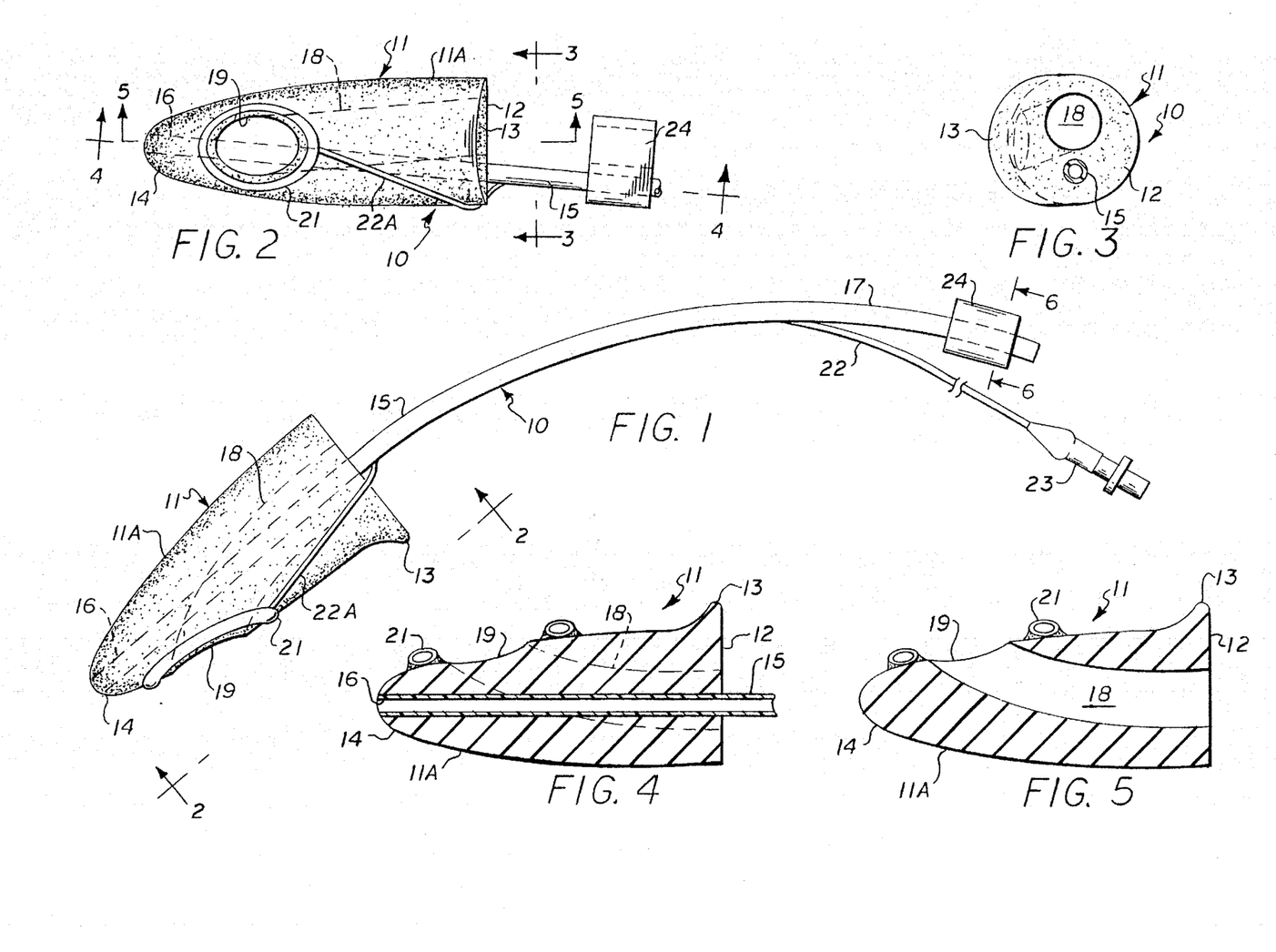
FIG. 1 is a side elevation of a preferred esophageal tracheal intubator airway device apparatus in accordance with the present invention.
FIG. 2 is a side view of the positioning element taken along line 2—2 of FIG. 1, showing the opening in its side wall surrounded by an inflatable ring.
FIG. 3 is a rear view of the proximal end of the positioning element.
FIG. 4 is a longitudinal cross section through the esophageal conduit secured in the positioning element taken along line 4—4 of FIG. 2.
FIG. 5 is a longitudinal cross section through the laryngeal channel of the positioning element taken along line 5—5 of FIG. 2, showing the inflatable ring inflated.

Referring to the drawings by numerals of reference, there is shown in FIGS. 1 and 2, a preferred esophageal tracheal intubator airway device 10. The esophageal tracheal intubator airway device 10 has a conical positioning element 11 formed of soft semi-flexible material, such as silicone rubber, which will conform to the interior surfaces of the patient's throat against which it is placed without traumatizing the throat. Referring additionally to FIGS. 2 and 3, the conical positioning element 11 has a generally flat rearward or proximal end 12 with a lip 13 extending radially outward to one side, a rounded tip 14 at the forward or distal end and a tapered side wall 11A.

One end of a relatively stiff but flexible tubular esophageal conduit 15 is secured within the conical positioning element 11 with its distal end 16 flush with the rounded tip 13 of the positioning element (FIG. 4). The mid section of the esophageal conduit 15 extends rearwardly from the conical positioning element 11 in a gently curved arcuate configuration. The interior diameter of the esophageal conduit 15 is sized to allow a standard gastric suction tube and other related medical instruments such as a fiberscope to pass slidably therethrough. The proximal end 17 of the esophageal conduit 15 serves as a handle for manually manipulating the conical positioning element 11.

Figure 8:
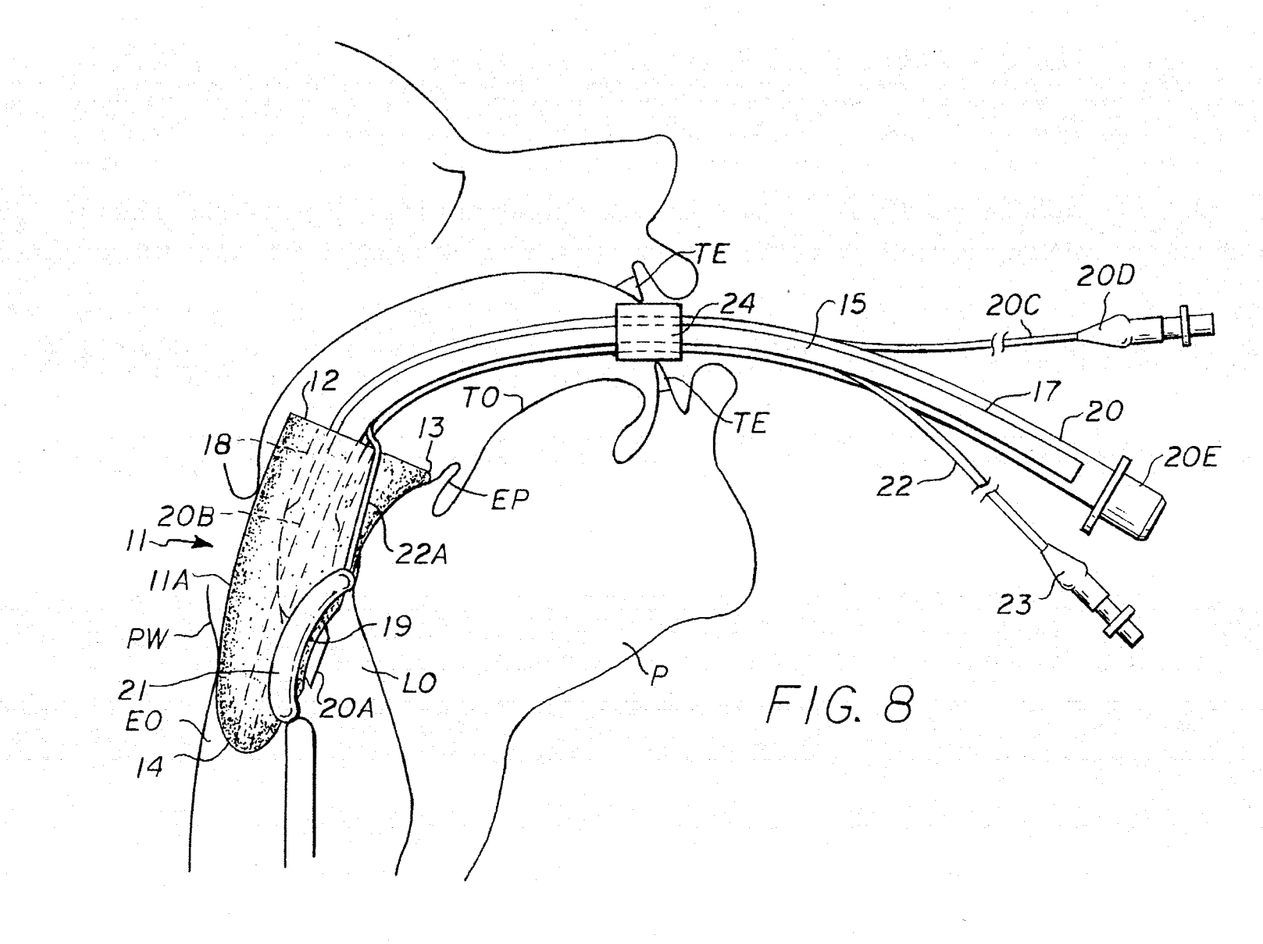
FIG. 8 is a side elevation of the esophageal tracheal intubator airway device and cuffed endotracheal tube installed in the throat of a patient.
Figure 9:
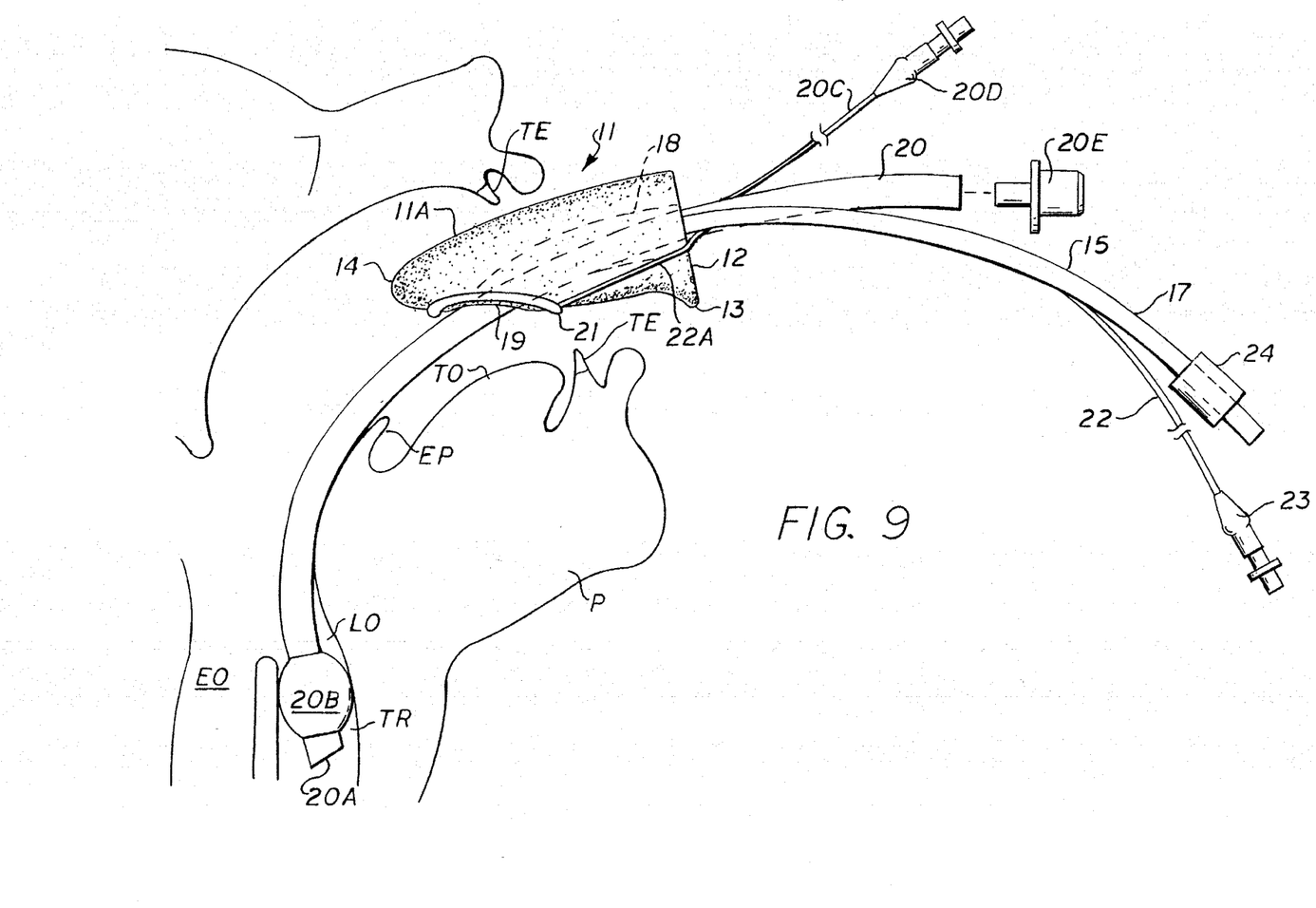
FIG. 9 is a side elevation of the esophageal tracheal intubator airway device being removed from the throat of the patient and leaving the cuffed endotracheal tube stabilized in the patient's trachea.

As best seen in FIG. 5, a laryngeal channel 18, positioned laterally to one side of the distal portion of the esophageal conduit 15, extends inwardly a distance from the proximal end 12 of the positioning element 11 and then curves outwardly to define an opening 19 through the side wall 11A of the conical positioning element. The interior diameter of the laryngeal channel 18 is sized to allow a standard cuffed endotracheal tube 20 ( as shown in FIGS. 7–9) or related instruments such as a fiberscope to pass slidably therethrough.

An inflatable generally oval-shaped tubular ring 21 is secured to the side wall 11A of the conical positioning element 11 and surrounds the opening 19. The inflatable ring 21 is formed of silicone rubber or other suitable material and has an outer periphery configured to form a sealing relation around the patient's laryngeal opening when the conical positioning element is properly positioned in the patient's throat and the ring is inflated. A small diameter air injection tube 22 is secured to the esophageal conduit 15 and its distal end 22A is connected with the inflatable ring 21 and its proximal end is provided with a conventional connector 23 for inflating the ring.

As explained hereinafter, the distal end of a standard endotracheal tube 20 is slidably received in the laryngeal channel 18 and during placement of the conical positioning element 11, the endotracheal tube is temporarily secured within the laryngeal channel with its distal end 20A flush with the opening 19 in the side wall 11A of the conical positioning element 11. In a preferred embodiment, the standard endotracheal tube 20 has a conventional inflatable cuff 20B surrounding its distal end which is inflated by means of the usual small diameter air injection tube 20C connected with the inflatable cuff and provided with a connector 20D at its proximal end for inflating the cuff. The cuff 20B of the endotracheal tube 20 may be inflated to engage the interior diameter of the laryngeal channel 18 to maintain the distal end 20A of the endotracheal tube flush with the opening 19 in the side wall of the conical positioning element 11.

Figures 6, 7:
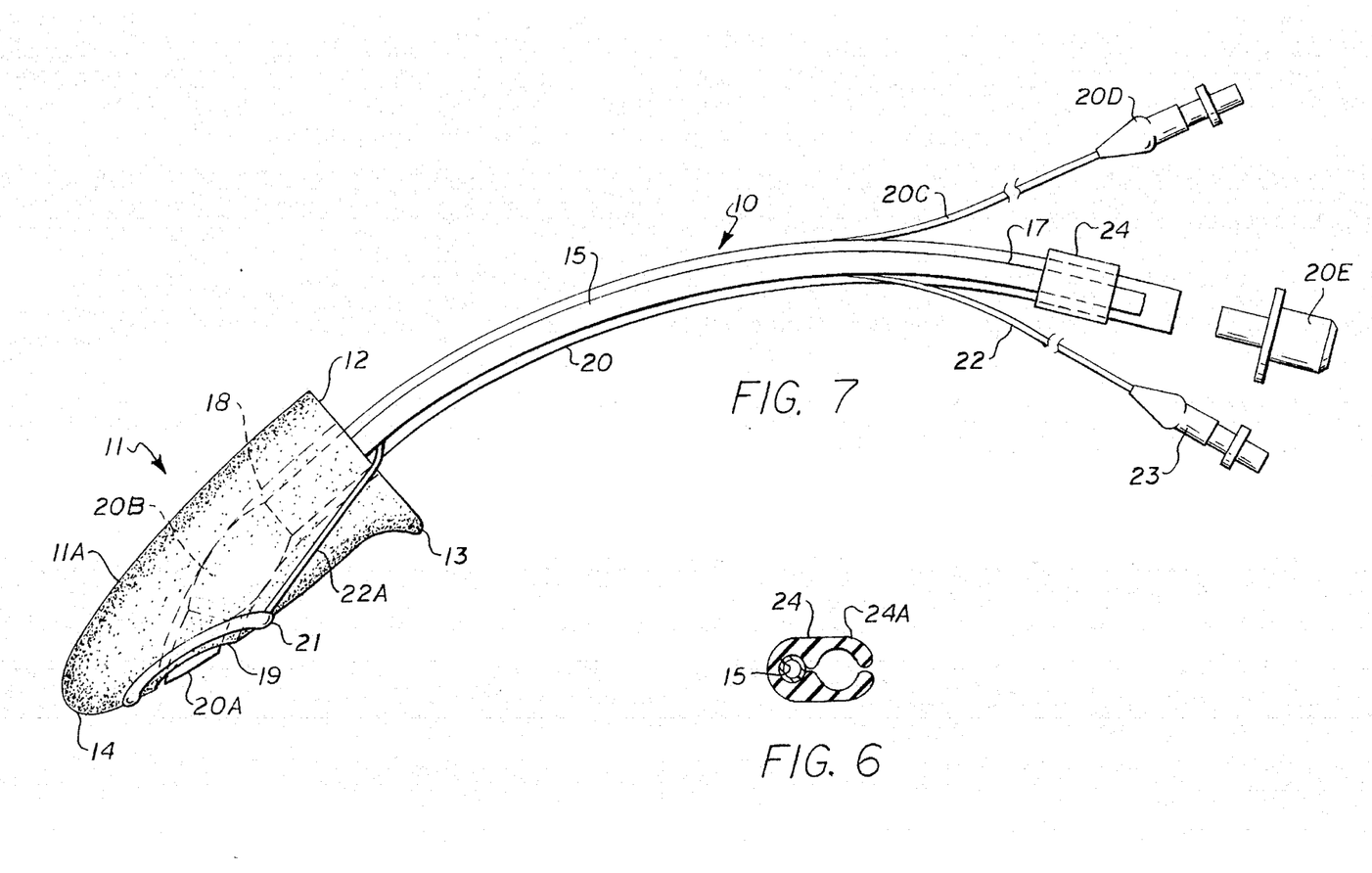
FIG. 6 is a cross sectional view of the clamp member of the esophageal tracheal intubator airway device.
FIG. 7 is a side elevation of the esophageal tracheal intubator airway device with a cuffed endotracheal tube installed in the laryngeal channel.

A clip 24 (FIG. 6) is attached to the esophageal conduit 15 near its proximal end 17 and has a laterally extending portion 24A which is configured to releasably receive and hold the proximal end of the endotracheal tube 20 in a position generally parallel to the esophageal conduit 15 (FIG. 7). The clip 24 can also be used to maintain the distal end 20A of the endotracheal tube 20 flush with the opening 19.

The preferred clip 24 is formed of a relatively stiff resilient material such as rubber or plastic which is sufficiently soft to prevent trauma to the teeth and gums while, at the same time, preventing the esophageal conduit 15 and endotracheal tube 20 or other instrument held by the clip from being compressed or damaged by the patient biting on them. In other words, the clip 24 also functions in the manner of a bite block.

Having thus described the structure of a preferred esophageal tracheal intubator airway device 10, a description of its operation follows with reference to FIGS. 7–9.

OPERATION

In intubating a patient P, an endotracheal tube 20 is inserted distal end first into the laryngeal channel 18 of the conical positioning element 11 until the distal end 20A of the endotracheal tube is flush with the opening 19 in the side wall 11A of the conical positioning element. If a conventional inflatable cuff endotracheal tube is being used, the cuff 20B surrounding its distal end is inflated to engage the interior diameter of the laryngeal channel 18 and maintain the distal end 20A of the tube 20 flush with the opening 19 in the side wall of the conical positioning element 11. The proximal end of the endotracheal tube 20 is clipped to the esophageal conduit 15 by the clip 24 to hold it in a position generally parallel to the esophageal conduit. The clip 24 can also be used to maintain the distal end 20A of the endotracheal tube 20 flush with the opening 19.

As shown in FIG. 8, the esophageal tracheal intubator airway 10 with the distal end of the endotracheal tube 20 installed therein is inserted, as a single unit, into the mouth of the patient P, past the teeth TE and over the tongue TO, and advanced along the midline of the mouth and downwardly along the posterior pharyngeal wall PW at the back of the throat until the tip 14 of the positioning element 11 enters as far as permitted by its shape into the esophageal opening EO. The ring 21 on the conical positioning element 11 is then inflated which causes the conical positioning element to back out slightly and its lip 13 to lift the tip of the epiglottis EP up and out of the way of the laryngeal channel opening 19 in the side wall 11A of the positioning element. The inflated ring 21 now comes to rest around the laryngeal opening LO. When the conical positioning element 11 is properly placed, its lip 13 at the proximal end 12 will be disposed just behind the epiglottis.

The clip 24 is then moved along the esophageal conduit 15 and endotracheal tube 20 and positioned between the upper and lower teeth T of the patient to function as a bite block to prevent the esophageal conduit 15 and endotracheal tube 20 from being compressed or damaged by the patient biting on them and to prevent trauma to the teeth and gums of the patient. Ventilation and stomach suction can now be performed through device as it is shown in FIG. 8.

The cuff 20B of the endotracheal tube 20 can then be deflated, and the distal end of the endotracheal tube can be pushed into the trachea TR of the patient, either blindly or over a fiberscope. The cuff 20B is then reinflated keeping the endotracheal tube in proper postion within the throat. At this point, ventilation can be carried out through the endotracheal tube 20 and stomach suctioning can be carried out by means of the esophageal conduit 15.

After the necessary procedures have been completed, the esophageal tracheal intubator airway 10 and the endotracheal tube 20 can be removed together, or, as shown in FIG. 9, the endotracheal tube 20 can be left in position, and the esophageal tracheal intubator airway 10 can be removed over the endotracheal tube 20 by unfastening the clip 24, removing the connector 20E at the proximal end of the tube 20, and pulling upwardly on the esophageal conduit 15 to slide the conical positioning element 11 along the length of the endotracheal tube and over the proximal end of the endotracheal tube.

While this invention has been described fully and completely with special emphasis upon a preferred embodiment, it should be understood that within the scope of the appended claims the invention may be practiced otherwise than as specifically described herein.

I claim:

1. An esophageal tracheal intubator airway device to facilitate rapid blind access to the larynx and esophagus of a patient for lung ventilation, stomach suctioning or fiberscopic examination of the upper respiratory and upper gastrointestinal tracts, and passage of an endotracheal tube into the trachea comprising:

a generally tapered positioning element receivable through the mouth having a distal end, a proximal end, and a side wall extending therebetween configured to conform with the base of the throat behind the epiglottis;

an elongate tubular esophageal conduit having a distal portion extending longitudinally through said positioning element and secured thereto with a distal tip end flush with said positioning element distal end, the remaining portion extending rearwardly from said positioning element proximal end in a gently curved arcuate configuration, and having an interior diameter of sufficient size to allow passage of a gastric suction tube and related medical instruments therethrough into the patient's esophagus;

a laryngeal channel in said positioning element extending inwardly a distance from its proximal end laterally adjacent said esophageal conduit and curving outwardly to define an opening through its said side wall;

said opening being positioned to become generally aligned with the patient's larynx when said positioning element is disposed in the base of the throat behind the epiglottis, and said laryngeal channel having an interior diameter of sufficient size to allow passage of a cuffed endotracheal tube and related medical instruments therethrough into the patient's larynx and trachea;

a generally oval-shaped inflatable tubular member secured to said positioning element side wall substantially surrounding said opening configured to form a sealing relation around the patient's laryngeal inlet when inflated; and an inflation tube having a distal end connected with said inflatable member and a proximal end adapted to be connected to inflation means for inflating said inflatable tubular member.

2. An esophageal tracheal intubator airway device according to claim 1 wherein said positioning element is formed of soft semi-flexible material which will conform to the interior surfaces of the patient's throat against which it is placed without traumatizing the throat.

3. An esophageal tracheal intubator airway device according to claim 1 wherein said positioning element is a generally conical-shaped positioning member having a rounded distal end and a tapered side wall diverging rearwardly therefrom and terminating in a wider proximal end.

4. An esophageal tracheal intubator airway device according to claim 1 wherein said esophageal conduit is formed of flexible material of sufficient stiffness to serve as a handle for manually manipulating said positioning element.

5. An esophageal tracheal intubator airway device according to claim 1 wherein said positioning element has a generally flat proximal end with an anterior lip extending radially outward to one side configured to engage the epiglottis.

6. An esophageal tracheal intubator airway device according to claim 4 wherein said inflatable tubular member is secured on the side wall of said positioning element a predetermined distance relative to said positioning element anterior lip and is sized and shaped to form a seal around the patient's laryngeal inlet in the inflated condition, and when inflated to push said positioning element and anterior lip outwardly relative to the throat distance sufficient to engage said anterior lip on the epiglottis and lift the tip of the epiglottis up and out of the way of said laryngeal channel opening on said positioning element side wall.

7. An esophageal tracheal intubator airway device according to claim 1 further comprising an endotracheal tube having a distal end slidably received in said laryngeal channel.

8. An esophageal tracheal intubator airway device according to claim 7 wherein said endotracheal tube has an inflatable cuff surrounding its distal end and an inflation tube having a distal end connected with said inflatable cuff and a proximal end adapted to be connected to inflation means for inflating said cuff, whereby said endotracheal tube may be temporarily secured within said laryngeal channel with its distal end flush with said opening in said positioning element side wall by inflating said cuff to engage the interior diameter of said laryngeal channel to facilitate insertion of said positioning element and said endotracheal tube as a single unit into the mouth of the patient and through the throat past the epiglottis until said positioning element comes to rest in the base of the throat, and after said inflatable tubular member is inflated, said cuff may be deflated and said endotracheal tube moved relative to said positioning element.

9. An esophageal tracheal intubator airway device according to claim 1 further comprising a clip means movably connected with said esophageal conduit near its proximal end and having a laterally extending portion configured to releasably receive and hold the proximal end of an endotracheal tube or related medical instrument in a position generally parallel to said esophageal conduit.

10. An esophageal tracheal intubator airway device according to claim 9 wherein said clip means is movable relative to said esophageal conduit and said endotracheal tube or related medical instrument held thereby to be positioned between the upper and lower teeth of the patient to function as a bite block, and said clip means is formed of relatively stiff resilient material sufficiently soft to prevent trauma to the teeth and gums while at the same time preventing said esophageal conduit and said endotracheal tube or related medical instrument held thereby from being compressed or damaged by the patient biting on them.

11. A method for rapid blind esophageal tracheal intubation of plural tubes from outside the mouth of a patient into the upper respiratory and upper gastrointestinal tracts, for lung ventilation, stomach suctioning or fiberscopic examination, and passage of an endotracheal tube into the trachea comprising the steps of:

providing a generally tapered positioning element having a distal end, a proximal end, and a side wall configured to conform with the base of the throat behind the epiglottis, an anterior lip extending radially outward to one side of said proximal end, an elongate tubular esophageal conduit having a distal portion extending longitudinally therethrough and a proximal portion extending rearwardly from said positioning element, a laryngeal channel in said positioning element extending inwardly a distance from said proximal end and curving outwardly to define an opening through said side wall, an inflatable tubular member secured to said side wall surrounding said opening configured to form a sealing relation around the patient's laryngeal inlet when inflated, and an inflation tube connected with said inflatable tubular member for inflating said inflatable tubular member;

said esophageal conduit having an interior diameter of sufficient size to allow passage of a gastric suction tube and related medical instruments therethrough into the patient's esophagus, and said laryngeal channel having an interior diameter of sufficient size to allow passage of an endotracheal tube and related medical instruments therethrough into the patient's larynx and trachea;

installing the distal portion of an endotracheal tube into said laryngeal channel and temporarily fixing its distal end flush with the opening in the side wall of said positioning element;

inserting said positioning element with said endotracheal tube installed, as a single unit, into the mouth of the patient, through the throat past the epiglottis until said positioning element distal end enters the esophageal opening and said anterior lip is disposed just behind the epiglottis with said inflatable tubular member around the patient's laryngeal inlet;

forming a seal around the patient's laryngeal inlet and lifting the tip of the epiglottis up and out of the way of said positioning element laryngeal channel opening by inflating said inflatable tubular member with sufficient pressure to form a seal around the laryngeal inlet and simultaneously cause said positioning element to back outwardly relative to the throat a sufficient distance to cause said anterior lip to engage and lift the tip of the epiglottis up and out of the way of said laryngeal channel opening on said positioning element side wall; and if stomach suction or fiberscopic examination is required, passing a gastric suction tube or related medical instrument through said esophageal conduit relative to said positioning element into the patient's esophagus or upper gastrointestinal tracts, as appropriate; and if lung ventilation or fiberscopic examination is required, passing said endotracheal tube or related medical instrument through said laryngeal channel relative to said positioning element into the patient's trachea or upper respiratory tract, as appropriate.

12. The method according to claim 11 wherein said step of installing said endotracheal tube comprises:

installing said endotracheal tube into said laryngeal channel with its distal end flush with the opening in the side wall of said positioning element;

installing the distal end of a fiberscope through said endotracheal tube; and thereafter moving said endotracheal tube and said fiberscope together or independently relative to one another and relative to said positioning element to pass said endotracheal tube and said fiberscope into the patient's trachea or upper respiratory tract, as appropriate.

13. The method according to claim 11 including the further steps of:

removing said gastric suction tube or related medical instrument by pulling it out of said esophageal conduit relative to said positioning element; and removing said endotracheal tube or related medical instrument by pulling it outward through said laryngeal channel relative to said positioning element.

14. The method according to claim 11 including the further steps of:

removing said gastric suction tube or related medical instrument by pulling it out of said esophageal conduit relative to said positioning element;

deflating said inflatable tubular member;

removing said positioning element by pulling it out of the patient's throat and mouth along the length of said endotracheal tube or related medical instrument and relative thereto until said laryngeal channel clears the proximal end thereof; and thereafter leaving said endotracheal tube or related medical instrument in the patient's trachea or upper respiratory tract for lung ventilation or fiberscopic examination, as appropriate.

15. A method for rapid blind esophageal tracheal intubation of plural tubes from outside the mouth of a patient into the upper respiratory and upper gastrointestinal tracts, for lung ventilation, stomach suctioning or fiberscopic examination, and passage of an inflatable cuff endotracheal tube into the trachea comprising the steps of:

providing a generally tapered positioning element having a distal end, a proximal end, and a side wall configured to conform with the base of the throat behind the epiglottis, an anterior lip extending radially outward to one side of said proximal end, an elongate tubular esophageal conduit having a distal portion extending longitudinally therethrough and a proximal portion extending rearwardly from said positioning element, a laryngeal channel in said positioning element extending inwardly a distance from said proximal end and curving outwardly to define an opening through said side wall, an inflatable tubular member secured to said side wall substantially surrounding said opening configured to form a sealing relation around the patient's laryngeal inlet when inflated, and an inflation tube connected with said inflatable tubular member for inflating said inflatable tubular member;

said esophageal conduit having an interior diameter of sufficient size to allow passage of a gastric suction tube and related medical instruments therethrough into the patient's esophagus, and said laryngeal channel having an interior diameter of sufficient size to allow passage of an inflatable cuff endotracheal tube and related medical instruments therethrough into the patient's larynx and trachea;

installing the distal portion of an inflatable cuff endotracheal tube into said laryngeal channel with its distal end flush with the opening in the side wall of said positioning element, and inflating the cuff of said inflatable cuff endotracheal tube to engage the interior diameter of said laryngeal channel and maintain said distal end flush with the opening in the side wall of said positioning element;

inserting said positioning element with said inflatable cuff endotracheal tube installed, as a single unit, into the mouth of the patient, through the throat past the epiglottis until said positioning element distal end enters the esophageal opening and said anterior lip is disposed just behind the epiglottis with said inflatable tubular member around the patient's laryngeal inlet;

forming a seal around the patient's laryngeal inlet and lifting the tip of the epiglottis up and out of the way of said positioning element laryngeal channel opening by inflating said inflatable tubular member with sufficient pressure to form a seal around the laryngeal inlet and simultaneously cause said positioning element to back outwardly relative to the throat a sufficient distance to cause said anterior lip to engage and lift the tip of the epiglottis up and out of the way of said laryngeal channel opening on said positioning element side wall; and if lung ventilation or fiberscopic examination is required, deflating said cuff of said inflatable cuff endotracheal tube and moving said inflatable cuff endotracheal tube relative to said positioning element to pass said inflatable cuff endotracheal tube through said laryngeal channel into the patient's trachea or upper respiratory tract or to remove said endotracheal tube from said positioning element, as appropriate; and if stomach suction or fiberscopic examination is required, passing a gastric suction tube or related medical instrument through said esophageal conduit relative to said positioning element into the patient's esophagus or upper gastrointestinal tracts, as appropriate.

* * * * *